US005527319A

United States Patent [19]
Green et al.

[11] Patent Number: 5,527,319
[45] Date of Patent: Jun. 18, 1996

[54] SURGICAL FASTENER APPLYING INSTRUMENT FOR LIGATING AND DIVIDING TISSUE

[75] Inventors: David T. Green, Westport; Henry Bolanos, East Norwalk; Thomas Alesi, New Fairfield, all of Conn.

[73] Assignee: United States Surgical Corporation, Norwalk, Conn.

[21] Appl. No.: 286,397

[22] Filed: Aug. 5, 1994

Related U.S. Application Data

[63] Continuation of Ser. No. 835,233, Feb. 13, 1992, abandoned.
[51] Int. Cl.⁶ .................................................. A61B 17/00
[52] U.S. Cl. .......................... 606/143; 606/139; 606/170
[58] Field of Search .................................... 606/139, 142, 606/143, 167, 170, 174, 190, 205, 207; 227/901, 19, 175

[56] References Cited

U.S. PATENT DOCUMENTS

| | | | |
|---|---|---|---|
| 3,006,344 | 10/1961 | Vogelfanger | 606/174 X |
| 3,631,707 | 1/1972 | Miller . | |
| 3,665,924 | 5/1972 | Noiles et al. . | |
| 3,735,762 | 5/1973 | Bryan et al. . | |
| 3,740,994 | 6/1973 | DeCarlo, Jr. . | |
| 3,777,538 | 12/1973 | Weatherly et al. . | |
| 3,882,854 | 5/1975 | Hulka et al. . | |
| 3,955,581 | 5/1976 | Spasiano et al. . | |
| 4,027,510 | 6/1977 | Hiltebrandt . | |
| 4,038,987 | 8/1977 | Komiya . | |
| 4,064,881 | 12/1977 | Meredith . | |
| 4,086,926 | 5/1978 | Green et al. . | |
| 4,152,920 | 5/1979 | Green . | |
| 4,169,476 | 10/1979 | Hiltebrandt . | |
| 4,196,836 | 4/1980 | Becht . | |
| 4,201,213 | 5/1980 | Townsend . | |
| 4,228,895 | 10/1980 | Larkin . | |
| 4,246,903 | 1/1981 | Larkin . | |

(List continued on next page.)

FOREIGN PATENT DOCUMENTS

WO9003763  4/1990  WIPO .

OTHER PUBLICATIONS

Swain et al., "An Endoscopic Stapling Device: The Development of a New Endoscopically controlled Device for Placing Multiple Transmural Staples in Gastrointestinal Tissue", Gastrointestinal Endoscopy, vol. 35, No. 4, 1989, pp. 338–339.
Swain et al., "An Endoscopic Sewing Machine", Gastrointestinal Endoscopy, vol. 32, No. 4, 1986, pp. 36–38.
"Stapling Techniques General Surgery", Third Ed., pp. 17–19 (1988).
"Auto Suture Powered LDS Disposable Surgical Stapler", Booklet (1990).
Swain et al., "Endoscopic Stapling in the Oesophagus and Stomach", The British Society of Gastroenterology, p. A599.
Swain et al., "Endoscopic Colostomy Gastrotomy and Anastomosis", The British Society of Gastroenterology, Item F82, p. A1004.
Swain et al., "Experimental Studies of New Mechanical Methods of Endoscopic Haemostasis: Stitching, Banding, Clamping and Ulcer Removal", The British Society of Gastroenterology, Item F20, p. A1151.
"Laparoscopic Sterilization with Spring Clips", by Jarostav Hulka, M.D., Published by Richard Wolf Medical Instruments Corp.

*Primary Examiner*—Stephen C. Pellegrino
*Assistant Examiner*—Jeffrey A. Schmidt

[57] ABSTRACT

An endoscopic ligating and dividing instrument includes an endoscopic portion and a non-endoscopic portion. The endoscopic portion includes clip closing jaws for applying at least two surgical clips to body tissue, pusher rods for loading clips into the jaws, a movable hook to catch and position the body tissue, and a knife for dividing the body tissue between the surgical clips. The non-endoscopic portion includes actuators responsive to manual actuation by a user.

53 Claims, 12 Drawing Sheets

U.S. PATENT DOCUMENTS

| | | | |
|---|---|---|---|
| 4,349,028 | 9/1982 | Green . | |
| 4,427,014 | 1/1984 | Bel et al. . | |
| 4,492,232 | 1/1985 | Green | 606/143 |
| 4,509,518 | 4/1985 | McGarry et al. . | |
| 4,512,345 | 4/1985 | Green . | |
| 4,556,058 | 12/1985 | Green | 606/143 |
| 4,562,839 | 1/1986 | Blake, III et al. . | |
| 4,569,346 | 2/1986 | Poirier . | |
| 4,576,165 | 3/1986 | Green et al. | 606/143 |
| 4,616,650 | 10/1986 | Green et al. . | |
| 4,624,254 | 11/1986 | McGarry et al. . | |
| 4,662,373 | 5/1987 | Montgomery et al. . | |
| 4,712,549 | 12/1987 | Peters et al. . | |
| 4,858,608 | 8/1989 | McQuilkin . | |
| 4,919,152 | 4/1990 | Ger . | |
| 4,944,443 | 7/1990 | Oddsen et al. . | |
| 5,026,375 | 6/1991 | Linovitz et al. . | |
| 5,040,715 | 8/1991 | Green et al. . | |
| 5,071,430 | 12/1991 | de Salis et al. . | |
| 5,084,057 | 1/1992 | Green et al. . | |
| 5,100,420 | 3/1992 | Green et al. . | |
| 5,104,394 | 4/1992 | Knoepfler . | |
| 5,156,608 | 10/1992 | Troidl et al. | 606/142 |
| 5,171,247 | 12/1992 | Hughett et al. | 606/142 |
| 5,171,250 | 12/1992 | Yoon | 606/142 |
| 5,207,691 | 5/1993 | Nardella | 606/142 |

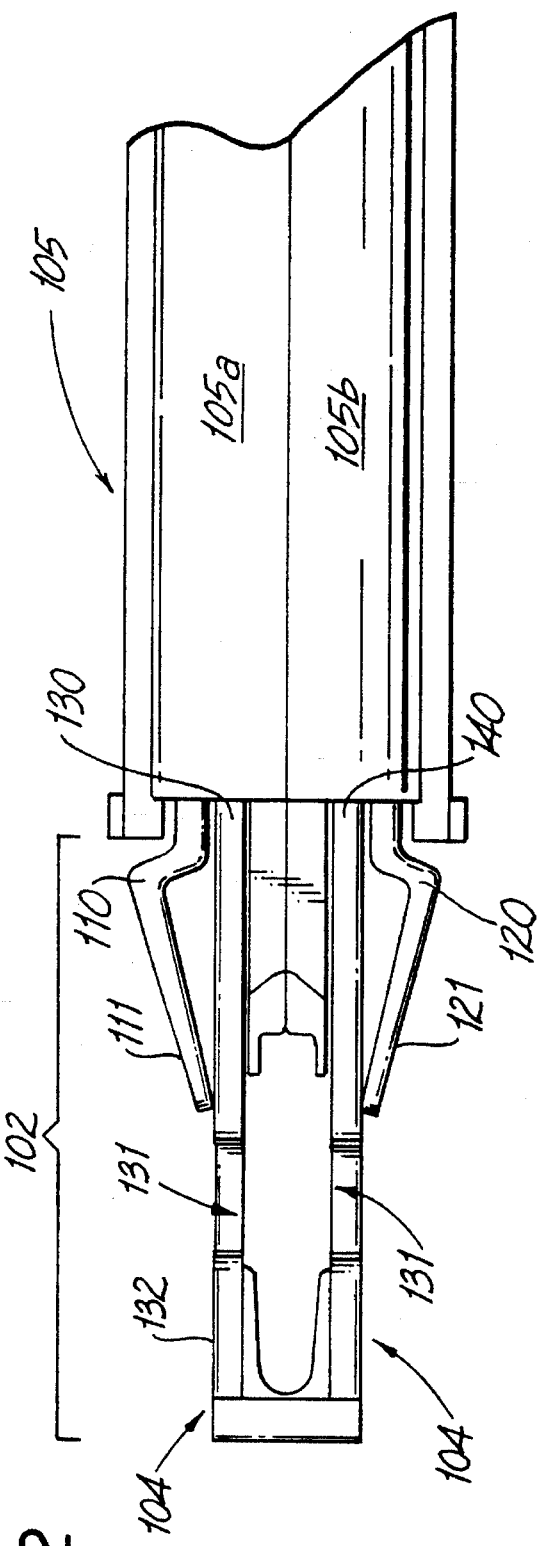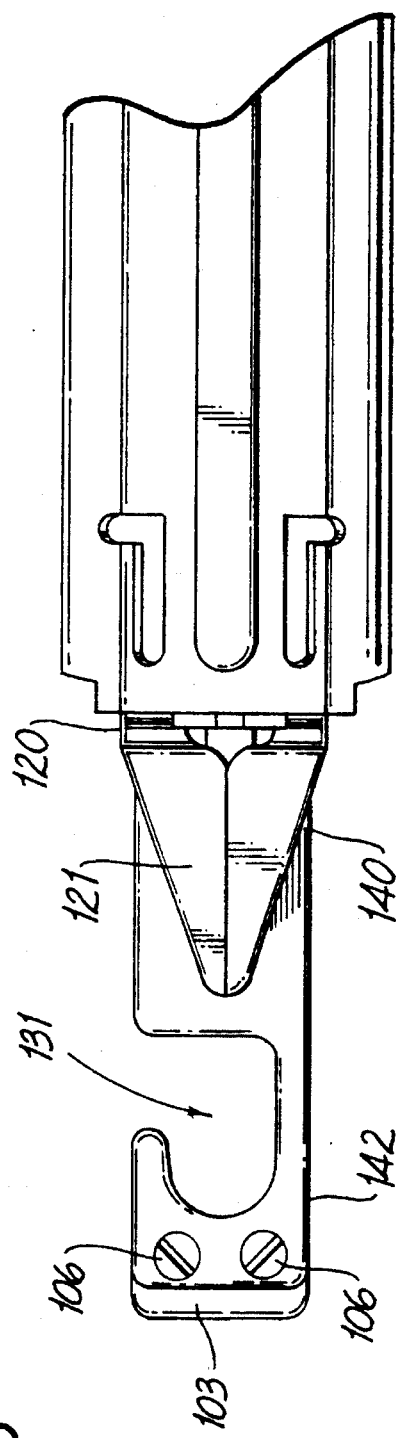
FIG. 2
FIG. 3

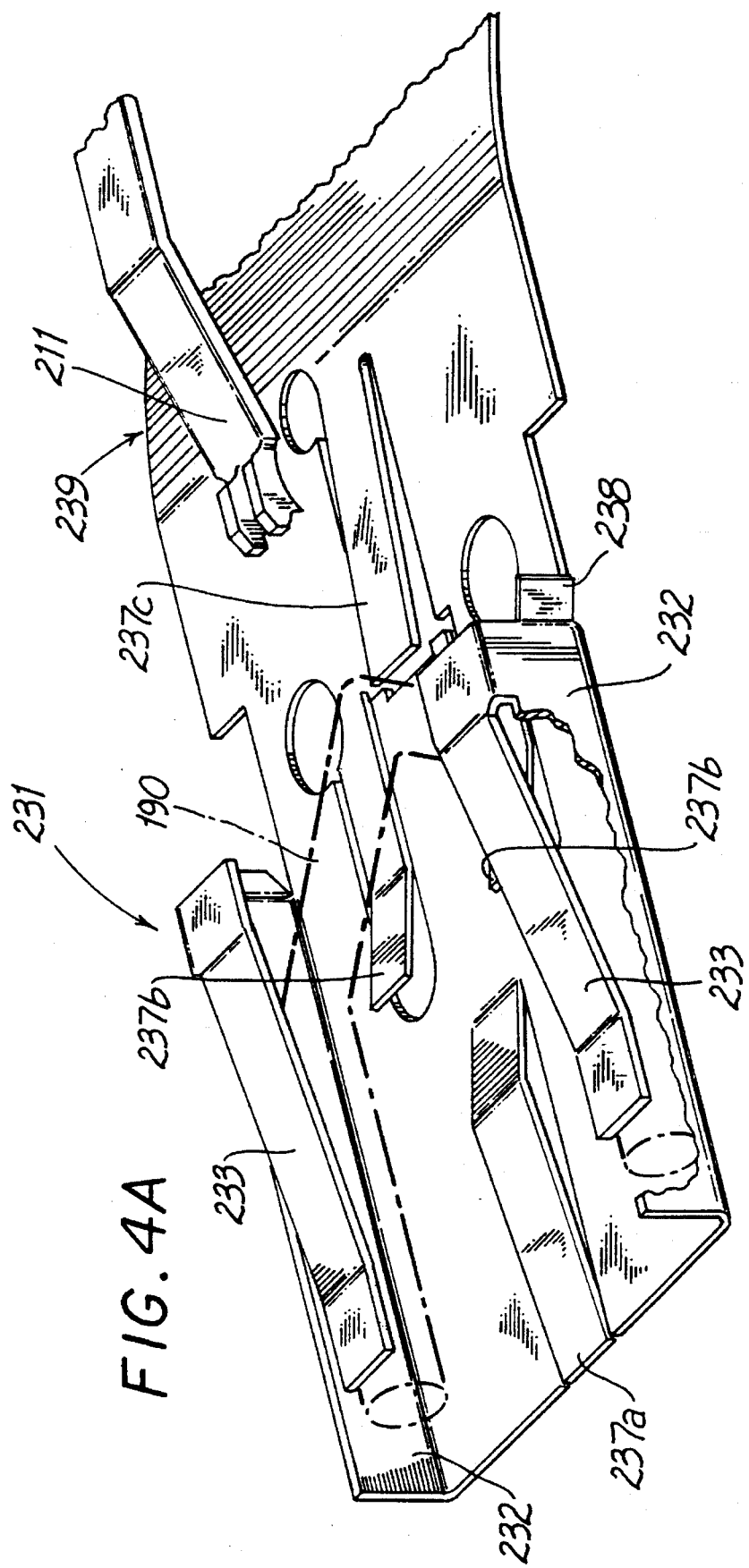

SURGICAL FASTENER APPLYING INSTRUMENT FOR LIGATING AND DIVIDING TISSUE

This is a continuation of application Ser. No. 07/835,233 filed on Feb. 13, 1992 now abandoned.

BACKGROUND OF THE INVENTION

1. Field of the Invention

The present invention relates to an apparatus for dividing body tissue, and more particularly to such an apparatus which may be employed to ligate and divide tubular vessels in endoscopic surgical procedures.

2. Background of the Art

Apparatus for ligating and dividing organic tubular structures (e.g., blood vessels and the like) are known and are commonly used in various surgical operations such as esophageal and gastric procedures. Generally such apparatus have a means for grasping the tubular structure, means for ligating the structure in two locations, usually by the application of staples, clips or the like, and means for dividing the tubular structure between the ligated portions, usually by slicing it with a knife.

U.S. Pat. No. 3,665,924 describes a ligating and dividing instrument which includes a cartridge for housing a plurality of staples. The instrument operates in three stages: after the tubular structure is inserted between the jaws of the cartridge, the cartridge jaws close, a pair of pushers come forward and suture the organic structure in two spaced locations with a pair of surgical staples, and a blade comes forward and divides the tubular structure. Other ligating and dividing instruments are disclosed in U.S. Pat. Nos. 4,086,926; 4,201,213; 4,349,028; and 4,556,058.

While the various known ligating and dividing apparatus have provided beneficial features to surgeons in the performance of non-endoscopic surgical operations, they are not useful in endoscopic or laparoscopic procedures. In laparoscopic procedures surgery is performed in the interior of the abdomen through a small incision. An endoscopic operation is one in which a surgical procedure is carried out in any hollow viscus of a human (or animal) body by means of instrumentation for operating or viewing deployed through one or more tubes. In either laparoscopic or endoscopic surgery, the functional portion of the instrumentation is manipulated or controlled from outside the body. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Laparoscopic and endoscopic procedures often require the surgeon to operate on organs, tissue, and vessels far removed from the site of the incision, thereby requiring that any instruments to be used in such procedures be both long and narrow. Mechanical actuation of such instruments is for the most part constrained to movement of the various components along a longitudinal axis, even if lateral movement is employed at the operating site. The initial opening in the body tissue to allow passage of the endoscopic tube to the interior of the body can be a natural passageway of the body (e.g. bronchial tubes), or it can be a puncture produced by a tissue piercing instrument such as a trocar. Because the endoscopic tubes, instrumentation, and any required puncture are relatively narrow, endoscopic surgery is less invasive and causes much less trauma to the patient as compared with surgery in which the surgeon is required to cut open large areas of body tissue. It would be advantageous to have an endoscopic ligating and dividing instrument, and we have developed an apparatus to meet this need.

SUMMARY

An apparatus is provided herein for endoscopically applying surgical fasteners, i.e., surgical clips to body tissue, the apparatus including an endoscopic portion which has a longitudinal axis and terminates in a distal end for positioning near the body tissue, and further having means for moving at least two fasteners longitudinally for applying the fasteners to the body tissue at spaced apart locations thereon.

More particularly, an apparatus is provided herein for endoscopically ligating and optionally dividing body tissue. The endoscopic portion of the apparatus includes clip closing means for substantially simultaneously applying at least two surgical clips to the body tissue at spaced apart locations, movable catch means to engage the body tissue and position said body tissue for operation by said jaw means, pusher means for individually advancing at least two surgical clips simultaneously to the clip closing means, knife means for cutting said body tissue at a position between said spaced apart locations of the clips, and a longitudinally extending tube for at least partially enclosing and supporting the clip closing means, pusher means, catch means, and knife means.

The clip closing means includes at least two pairs of opposing jaws, each pair being laterally movable between an open position wherein the jaws of each pair are spaced apart a relatively wider distance and a closed position wherein the jaws of each pair are in close proximity to each other. Each of the jaws possesses at least one camming surface. The jaws can distally extend from one member. Preferably, each pair of jaws extend distally from a separate member. Each pair of jaws is mounted to and integrally constructed with a corresponding pair of prong portions of the member, the pairs of jaws being resiliently biased to said open position.

A supply of clips is preferably stored in two parallel, longitudinally oriented rows in the endoscopic tube. The pusher includes means for moving the furthest clip at the distal end of each of said two rows into position in the clip closing means.

The knife means includes an elongated member having distal and proximal ends and extending longitudinally through the tube and a tissue cutting blade mounted to the distal end of the elongated member. The tissue cutting blade is movable between a distal position and a proximal position.

The catch means includes at least two elongated members, each having a distal end portion and a proximal end portion, each member being longitudinally movable between a proximal position and a distal position, and each member having a tissue reception space defined by a hook configuration of said distal end portion. The distal end portions are fixedly attached to a spacer member located therebetween, and the proximal end portion are connected to the catch actuation means.

The pusher means includes at least two elongated members, each being longitudinally movable between a proximal position and a distal position, and each having a distal end portion and a proximal end portion.

The non-endoscopic portion of the apparatus includes a housing, which supports and at least partially encloses a knife actuation means, catch actuation means, pusher actuation means, and jaw actuation means.

The proximal end of the elongated member of the knife means is connected to the knife actuation means and the knife actuation means is distally movable between a proximal position and a distal position in response to user applied pressure. The knife actuation means is preferably biased by resilient means to the proximal position.

The catch actuation means includes a member slidably mounted to the housing, the member being longitudinally movable between a proximal position and a distal position in response to user applied pressure.

The pusher actuation means includes a member slidably mounted to said housing, said member being longitudinally movable between a proximal position and a distal position in response to user applied pressure. Preferably, the pusher actuation means is biased by resilient means to the proximal position.

The jaw actuation means includes at least one elongated member having a distal end portion and a proximal end portion, the distal end portion including at least one edge for contacting the camming surfaces of the jaws and urging the respective pairs of jaws laterally inward to the closed position, the elongated member(s) being longitudinally movable between a distal position wherein the pairs of jaws are cammed to the closed position and a proximal position wherein the pairs of jaws are in the open position.

The jaw actuation means further includes trigger means connected to the proximal end portion of the elongated member(s) of the jaw actuation means, the trigger means being movable between a jaw opening position and a jaw closing position in response to a user applied force. The trigger means is pivotally mounted to the housing such that movement of the trigger means from said jaw opening position to said jaw closing position advances the elongated member(s) of the jaw actuation means to the distal position wherein said jaws are cammed closed.

BRIEF DESCRIPTION OF THE DRAWINGS

FIGS. 2 and 3 are, respectively, plan and side elevational views of the distal portion of the apparatus.

FIG. 4a is a detailed perspective view of the distal portion of the track member.

DETAILED DESCRIPTION OF PREFERRED EMBODIMENT(S)

1. Preface

An endoscopic clip applier is described in U.S. application Ser. No. 07/381,265 filed on Jul. 18, 1989 and herein incorporated by reference.

In the following description it should be noted that such terms as "distal" and "proximal", "upper" and "lower", "horizontal" and "vertical", "above" and "below", are used relative to each other and do not refer to positions or orientations relative to an external frame of reference. The term "endoscopic" as used herein with reference to apparatus and procedures shall also encompass laparoscopic apparatus and procedures.

Because endoscopic procedures are more common than laparoscopic procedures, the present invention shall be discussed in terms of endoscopic procedures and apparatus. However, use herein of terms such as "endoscopic", "endoscopically" and "endoscopic portion", among others, refer generally to instruments having elongated and relatively narrow operating portions for inserting into a cannula, body opening, or small wound in the skin and should not be construed to limit the present invention to an apparatus for applying surgical clips only in conjunction with an endoscopic tube. To the contrary, the present invention may find use in any procedure where access is limited to a small incision or body opening, including, but not limited to laparoscopic procedures.

2. Overview of the Apparatus

Figure 1:
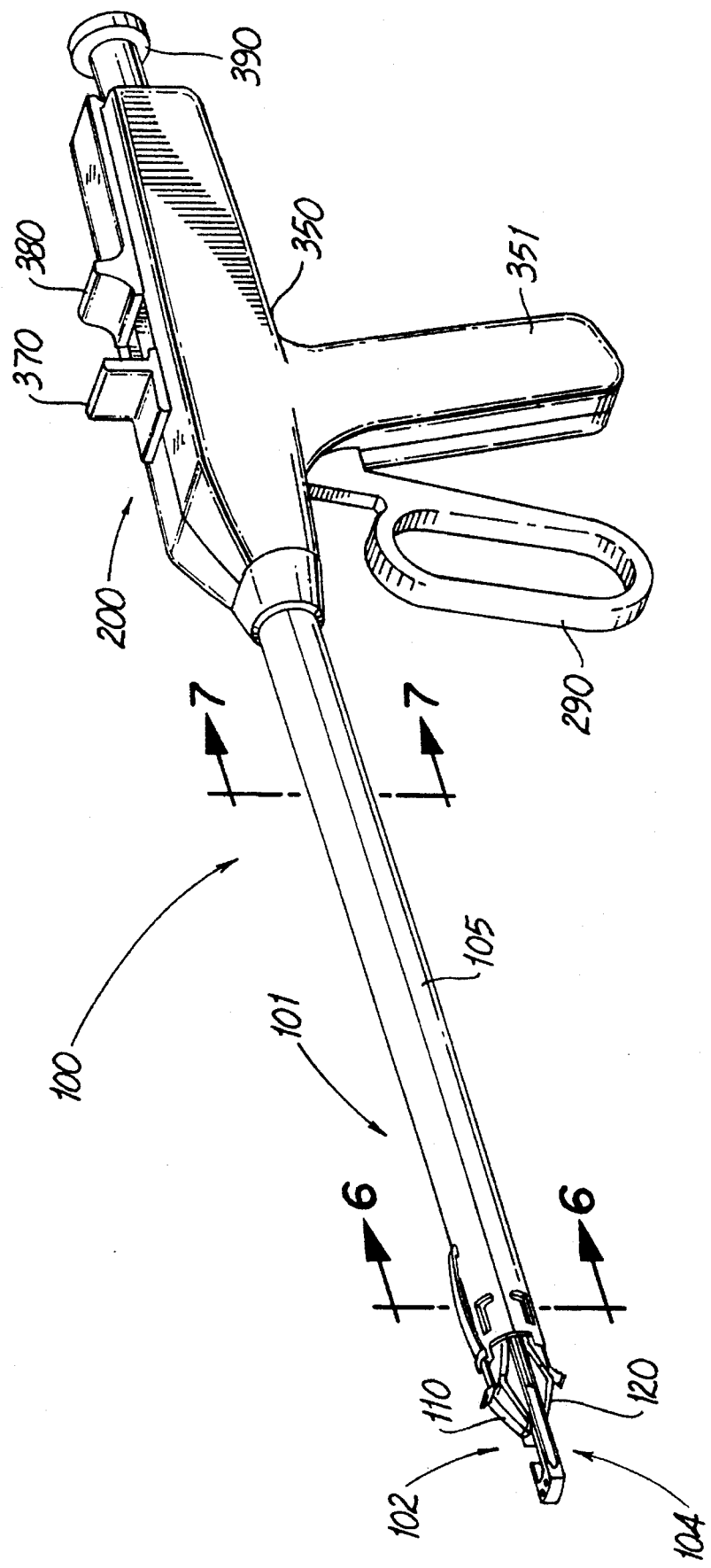
FIG. 1 is a perspective view of the ligating and dividing apparatus of the present invention.

FIG. 1, illustrates a preferred embodiment of the apparatus of the present invention. The apparatus is preferably constructed as a disposable item of several materials as will be described. Essentially, however, two basic materials are used: a polycarbonate plastic such as LEXAN brand polycarbonate produced by General Electric Company, and stainless steel. Polycarbonate is a high strength polymer which exhibits superior dimensional stability even under relatively high stresses, and is also biologically compatible.

Briefly, the apparatus 100 includes an endoscopic portion 101, having an operating portion 102 and a non-endoscopic portion 200. The endoscopic portion is of such diameter so as to be insertable into a cannula inserted through a wall of body tissue for operation at an operating site in the interim of the human (or animal) body. The apparatus is manipulated to locate the operating portion 102 in position for operating on the body tissue. The non-endoscopic portion 200, which remains outside the body, has the various actuators which the surgeon employs to perform the operation. After the operation is completed, the apparatus 100 is withdrawn. The apparatus is intended to be disposed of after the operation.

Figure 4:
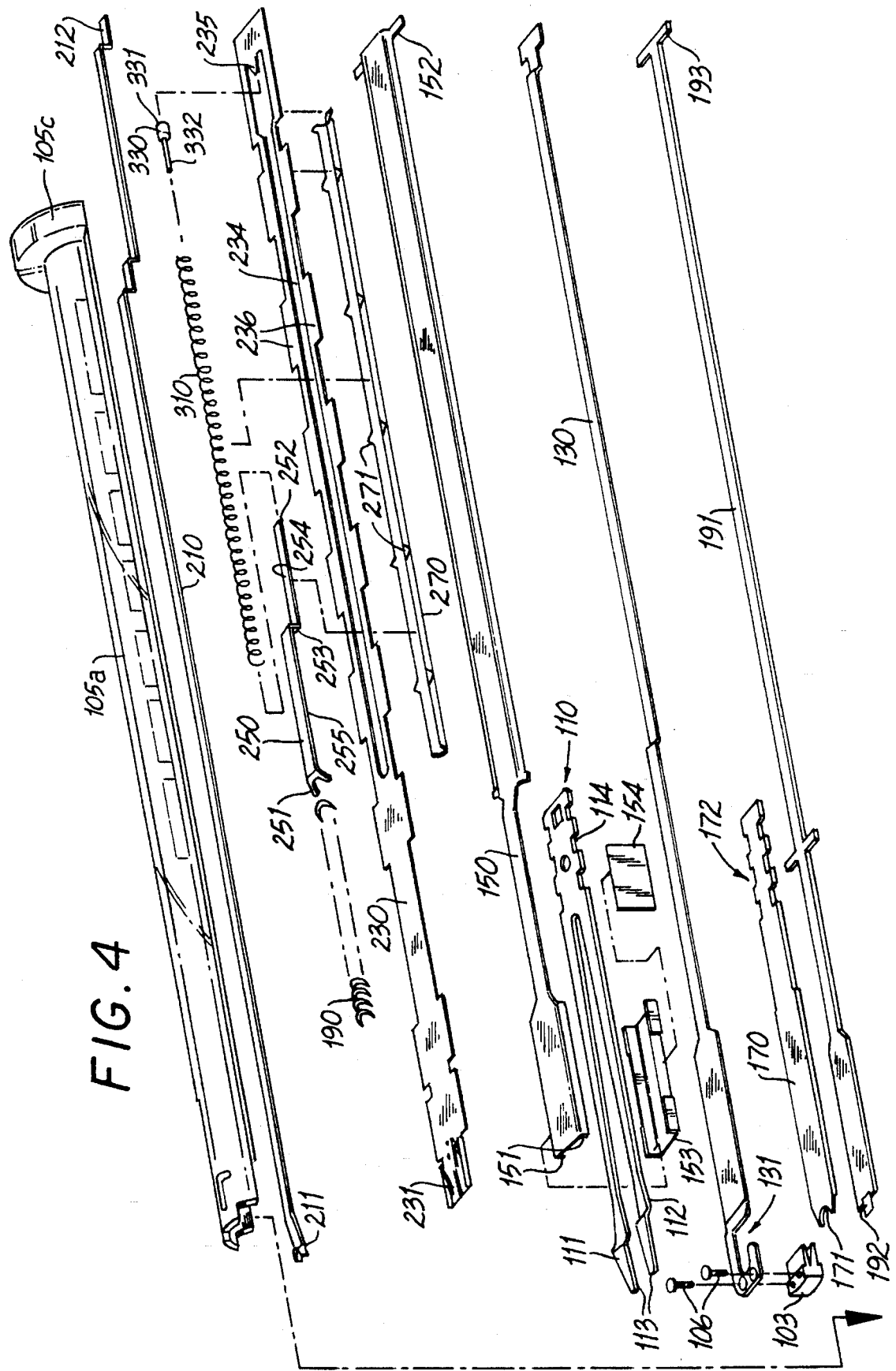
FIGS. 4 and 5 are exploded perspective views of the endoscopic portion of the apparatus.
Figure 5:
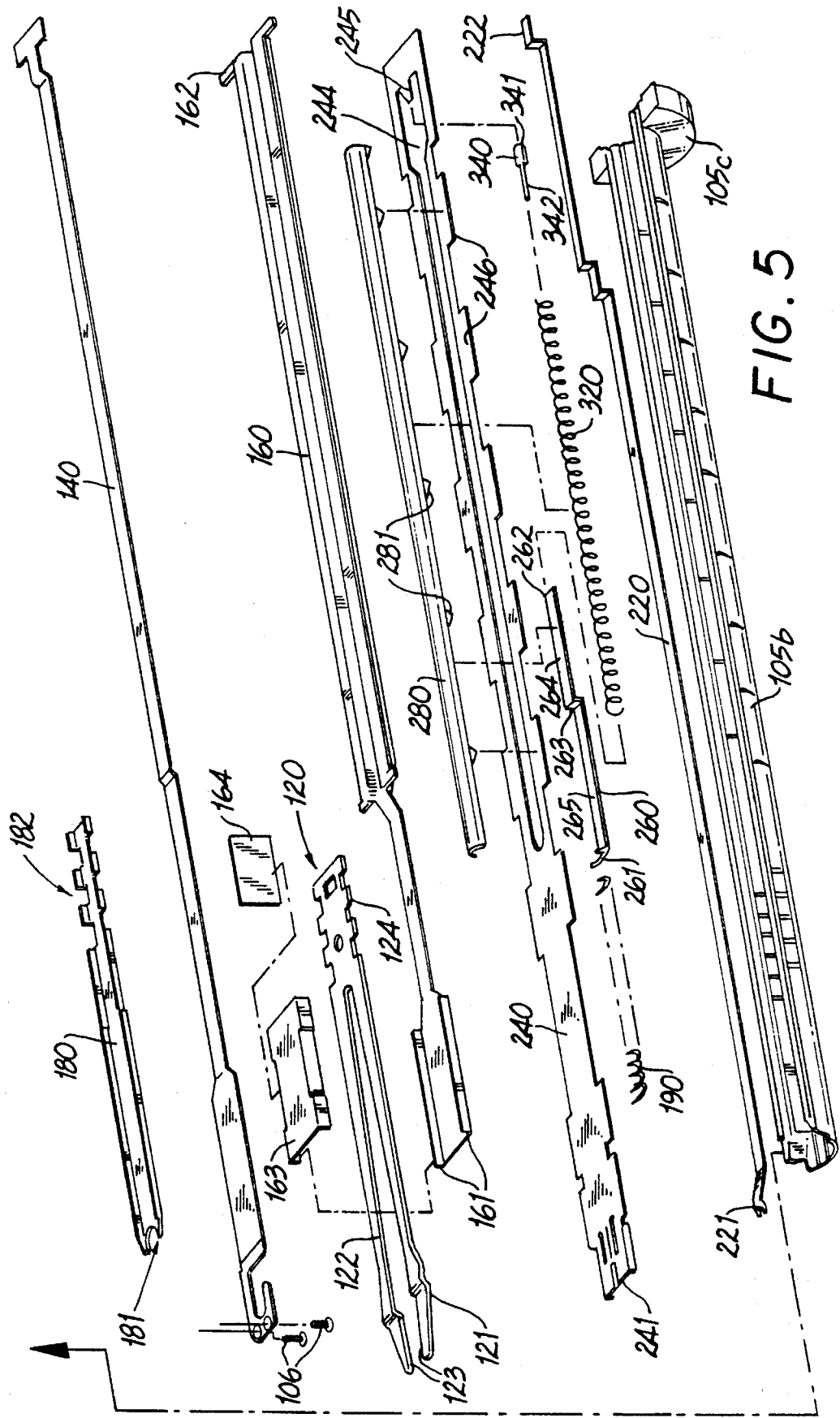
Figure 6:
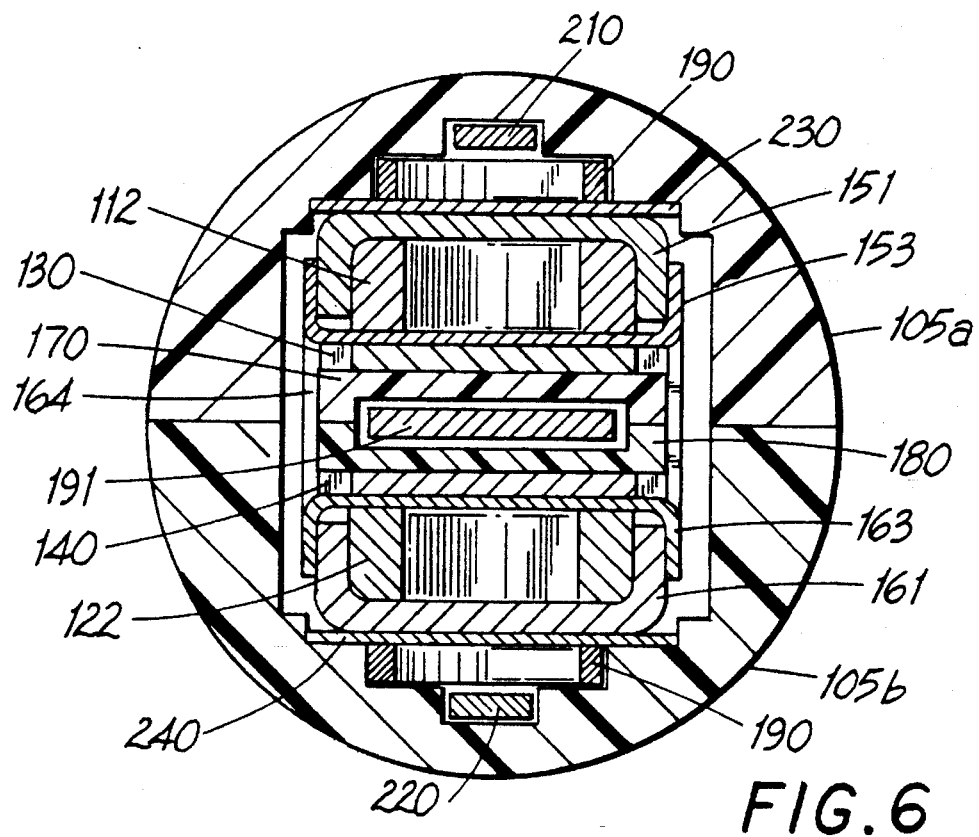
FIGS. 6 and 7 are sectional view of the endoscopic portion of the apparatus.
Figure 7:
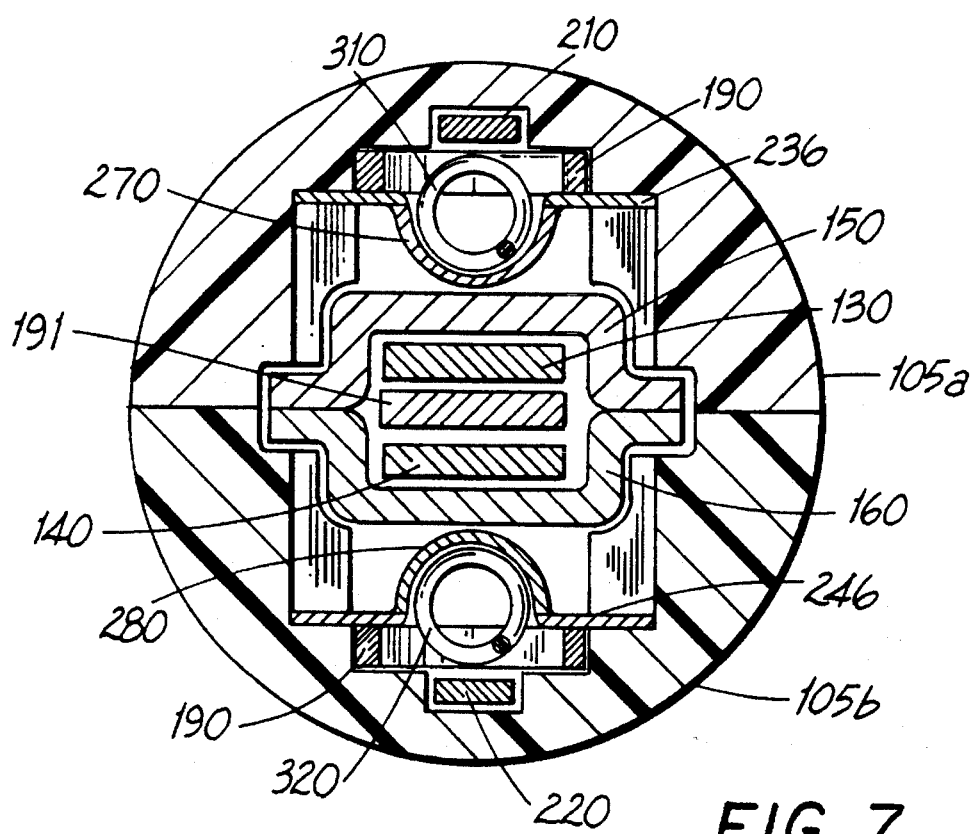

The clips 190 (See FIGS. 4, 4a, and 5) are preferably fabricated from a strong flexible and ductile material capable of undergoing deformation without breaking, and which is suitable for use in surgical applications without causing adverse body reactions, i.e., it must be biocompatible. Metals are usually used for fabricating such clips, and commonly used metals include stainless steel, tantalum, and titanium. Polymeric materials may also be used provided they have the requisite mechanism and biological properties. Clips of generally U-shape or V-shaped configuration of the type generally suitable for use in the apparatus described herein are described in U.S. Pat. Nos. 4,976,722; 4,844,066; 4,188,953; and 3,363,628.

3. The Endoscopic Portion

Referring to FIGS. 1, 2, and 3 an embodiment of the endoscopic ligating and dividing instrument of the present invention comprises an endoscopic portion 101 and a non-endoscopic actuation portion 200. At the distal end of the endoscopic portion 101 is the operating portion 102 which includes tissue grasping assembly 104 having hook members 130 and 140 for grasping and pulling tubular organic body tissue, means such as movable clip closing means 110 and 120 for applying at least two clips to the tubular organic body tissue at spaced apart positions, means such as clip pushers 210 and 220 for loading at least one clip 190 (FIGS. 4 and 5) into each clip closer, and means such as knife 191 (FIG. 4) for cutting the tissue at a position between the two clips.

The non-endoscopic portion 200 of the apparatus (FIG. 1) includes hook retractor means 380, clip loader actuation means 390, clip closer actuation means 290, and knife actuation means 370, as well as housing 350 and handle means 351 for support by the user.

Referring now to FIGS. 2, and 3, which illustrate the operating portion 102 of the instrument, tissue grasping assembly 104 includes hook members 130 and 140 which are flat members with distal end portions 132 and 142 each having an opening 131 for receiving body tissue, as will be illustrated below. Screws 106 fasten the distal end of the hook members to an anvil or spacer member 103 located between them at the distal end of the apparatus 100.

Clip closers 110 and 120 each include a pair of jaws 111 and 121, respectively, which project distally from the elongated outer tube 105. The outer tube 105 is adapted to fit through the cannula of a trocar assembly during an endoscopic surgical procedure. Outer tube 105 comprises upper and lower portions 105a and 105b which are adapted to fit together. When the apparatus is assembled, the upper and lower portions 105a and 105b may be bonded together by adhesive or other means, or they may be fabricated so as to snap fit together for secure joining. The proximal end of outer tube 105 possesses a circumferential flange 105C to facilitate mounting to the non-endoscopic portion 200.

Referring to FIGS. 4, 4a, 5, 6, and 7, clip pushing rods 210 and 220 each comprise an elongated member having a distal end portions 211 and 221, respectively, for individually advancing a clip 190 at the distal end of a row of clips into a respective pair of jaws 111 and 121. Rods 210 and 220 also each have a proximal end 212 and 222, respectively, for mounting to an actuator, discussed below. Clip tracks 230 and 240 for clips 190 are elongated members which serve to orient the respective rows of clips 190 longitudinally along the axis of the endoscopic portion 102. Tracks 230 and 240 each include a longitudinally extending slot 234 and 244, respectively, and a mounting post 235 and 245, respectively. Also included on the tracks are wing-like projections 236 and 246, respectively, which fit into corresponding slots in the outer tube 105 so as to secure the tracks in a fixed position relative to the instrument. The tracks include distal ends 231 and 241, respectively, which are described in more detail below with reference to FIG. 4a.

Spring retainer pins 330 and 340 are mounted on mounting posts 235 and 245, respectively, by means of apertured rear or proximal portion 331 and 341, respectively. Each spring retainer pin 330 and 340 possesses a distally extending pin portion 332 and 342, respectively, to which springs 310 and 320 are mounted. Springs 310 and 320 provide biasing force to urge the rows of clips 190 distally forward. Clip row advances 250 and 260 are elongated members each having a proximal end 252 and 262, respectively, for mounting to the distal end of springs 310 and 320, respectively. The distal end 251 and 261 of the clip row advancers is forked and is configured and dimensioned so as to engage the rear (proximal-most clip in the row of clips. Clip row advancers 250 and 260 each have a bend 253 and 263 dividing the advancers into two portions: a proximal portion 254,264 which is located at one side of the respective clip tracks 240, 250 and engages the respective one of the springs, and a distal portion 255, 265 which is located on the opposite side of the respective clip track where the clip row is located. Thus, bend portion 253 and 263 ride through slots 234, 244, respectively.

Attached to clip tracks 230 and 240 are channel members 270 and 280, which mount to the sides of the track members opposite that upon which the clips 190 ride. Channel members 270 and 280 possess flaps 271 and 281 which are preferably spot welded to wings 236 and 246 of the tracks. As can be seen from FIGS. 4 and 5, the channel members 270 and 280 are configured so as to form an elongated longitudinally extending channel of substantially semicircular cross section. The springs 310 and 320 are mounted in these channels. The proximal portions 254 and 264 also ride in the channels formed by channel members 270 and 280, respectively. Bends 253 and 263 enable the clip row advancers 250 and 260 to exert distal biasing force on the clips, which are located on the other side of the track member.

Referring to FIG. 4a, distal portions 231 and 241 of the respective track members 230 and 240 include side walls 232 to which spring clips 233 are attached, escapement 237a, 237b, and 237c, and guide flaps 238. The escapements provide for sequential advancement of the clips, i.e., the escapements limit the advancement of the clips 190 to one clip at a time. Thus, the distal-most clip passes over proximal escapement 237c and lodges between escapement 237c and escapements 237b. Spring clips 233 contact the legs of the clip and maintain it in position as it is advanced to the jaws 111 and 121. A novel feature of the present invention is that the distal portions 231 and 241 are resiliently flexible and bend at location 239. This feature enables the distal portions 231 and 241 to occupy the same space as the distal portion of the camming members 150 and 160 (discussed below), but at a different time. Thus, distal portions 231 and 241 are positioned so as to align the clips 190 with the jaws 111, 121 when the clips are advanced to the jaws. However, when the jaws 111, 121 are closed by advancing the camming members 150 and 160, the distal portions 231 and 241 flex outwardly to get out of the way of the camming members. This arrangement allows the construction of an endoscopic section with a smaller diameter than that which would be required if the distal portions 231 and 241 were not resiliently bent towards the center.

The jaws 111 and 121 are mounted to distally projecting resilient pairs of prongs 112 and 122, respectively, and each jaw possesses a notch 113 and 123, respectively, for holding the leg of a clip 190. The pairs of prongs 112 and 122 are initially in a spread apart configuration such that the pairs of jaws 111 and 121 are biased to the open position when pressure is applied by camming means. However, because of their flexibility, the pairs of prongs 112 and 122 bend laterally inward to permit closing of the pairs of jaws. The jaw members 110 and 120 each have crenelated end portion, 114 and 124, respectively, which is adapted to fit in a corresponding crenelated portion of the tubular members 105a, 105b in order to secure the position of the jaw members 110 and 120 relative to the instrument. The closing of the pairs of jaws is accomplished by distally moving camming members 150 and 160 which contact camming surfaces 114 and 124, respectively, to force the jaws 111 and 121 inward.

Camming members 150 and 160 each comprise an elongated camming member having distal camming edges 151 and 161, respectively. Laterally extending bars 152, 162 connect the proximal ends of camming members 150 and 160 to the trigger 290 as explained below.

The camming members 150 and 160 each have an inner plate 153 and 163, respectively. Side plates 154 and 164 join the distal end portions of the camming members 150 and 160 to form a box-like structure. Jaw member 110 is disposed through the space defined by the conjunction of camming member 150 and inner plate 153, and jaw member 120 is disposed through the space defined by the conjunction of camming member 160 and inner plate 163.

Knife covers 170 and 180 each include a tissue stopping distal edge 171 and 181, respectively, for preventing body tissue from moving proximally beyond the range of the jaws 111 and 121. Knife covers 170 and 180 each further include a proximal end portion having a plurality of lateral projections 172, 182, respectively, for facilitating mounting to the interior of the tube 105. The knife covers are in a fixed position relative to the instrument and do not move. The knife covers mount together to form a chamber through which knife 191 slides. The knife covers 170 and 180 may be fabricated from a polymer such as polycarbonate plastic.

Knife member 191 is an elongated member which includes distal knife edge 192 for cutting tissue. Knife 191 is longitudinally slidable within the tube 105 and members 150 and 160.

Figure 8:
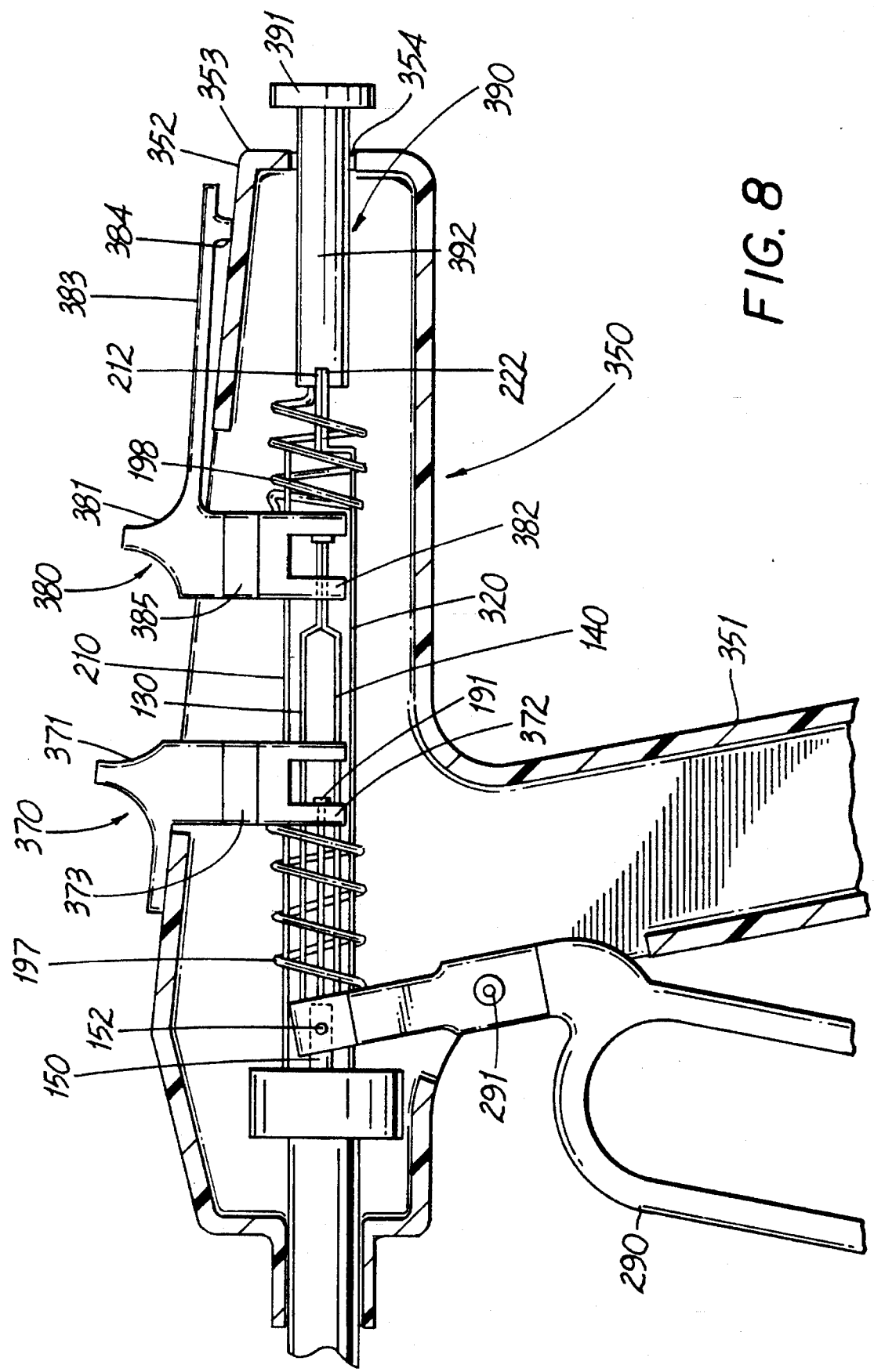
FIG. 8 is a cutaway side elevational view of the handle portion of the apparatus.

Referring to FIG. 8, the non-endoscopic portion 200 of the apparatus includes housing 350 which includes handle portion 351 to provide gripping means for the user.

Trigger 290 is pivotally mounted to the housing 350 by pivot pin 291. The top of the trigger is pivotally mounted to the proximal end of the camming members 150 and 160 by means of lateral bar 152 such that when trigger 290 is pivoted towards handle 351, the camming members 150 and 160 are advanced distally to close jaws 111 and 121.

Knife advancing actuator 370 is slidably mounted to housing 350 and movable between a distal and proximal position. Its upper portion projects outside the housing 350. The upper portion of knife advancing actuator 370 includes an upper surface 371 for receiving pressure applied by a user's finger(s). Knife advancing actuator 370 also includes a lower portion 372 which is mounted to the proximal end 193 of knife 191. Spring 197 biases the knife advancing actuator 370 to a proximal position. At least one laterally projecting detent 373 rides in a corresponding longitudinally extending slot in the inside surface of housing 350, which provides a guide pathway for longitudinal movement of the knife advancing actuator 370.

Hook retracting actuator 380 is slidably mounted to housing 350 and movable between a distal and proximal position. Hook retracting actuator 380 has an upper portion projecting outside the housing 350 and an upper surface 381 for receiving pressure applied by a user's finger(s). The lower portion of the hook retracting actuator 380 is mounted to the proximal end of hook members 130 and 140. The upper portion of the hook retracting actuator 380 includes a flat proximal projection 383 having a lower detent 384. The projection is of such length that when the hook retracting actuator is pulled back to its proximal position the detent 384 rides down the upper rear surface 352 of housing 350 and resiliently snaps down over the proximal edge 353 to lock the hook in the rear proximal position. Hook retracting actuator 380 also includes at least one laterally projecting detent 385 which rides in a corresponding longitudinally extending slot in the inside surface of housing 350, which provides a guide pathway or longitudinal movement of the hook retracting actuator 380.

Clip advancing actuator 390, i.e. a clip pusher actuator is slidably mounted to the housing 350 and at least partially extends through aperture 354 in the housing thereby presenting surface 391 for receiving pressure from the user's finger(s). The clip advancing actuator is movable between a distal position and a proximal position and is attached at its distal end 392 to the proximal ends 212 and 222 of clip pushers 210 and 220. Spring 198 abuts the distal end 392 of the clip advancing actuator 390 and biases actuator 390 towards the proximal direction. The distal end of spring 198 abuts the proximal surface of the hook retraction actuator 380.

Figure 9:
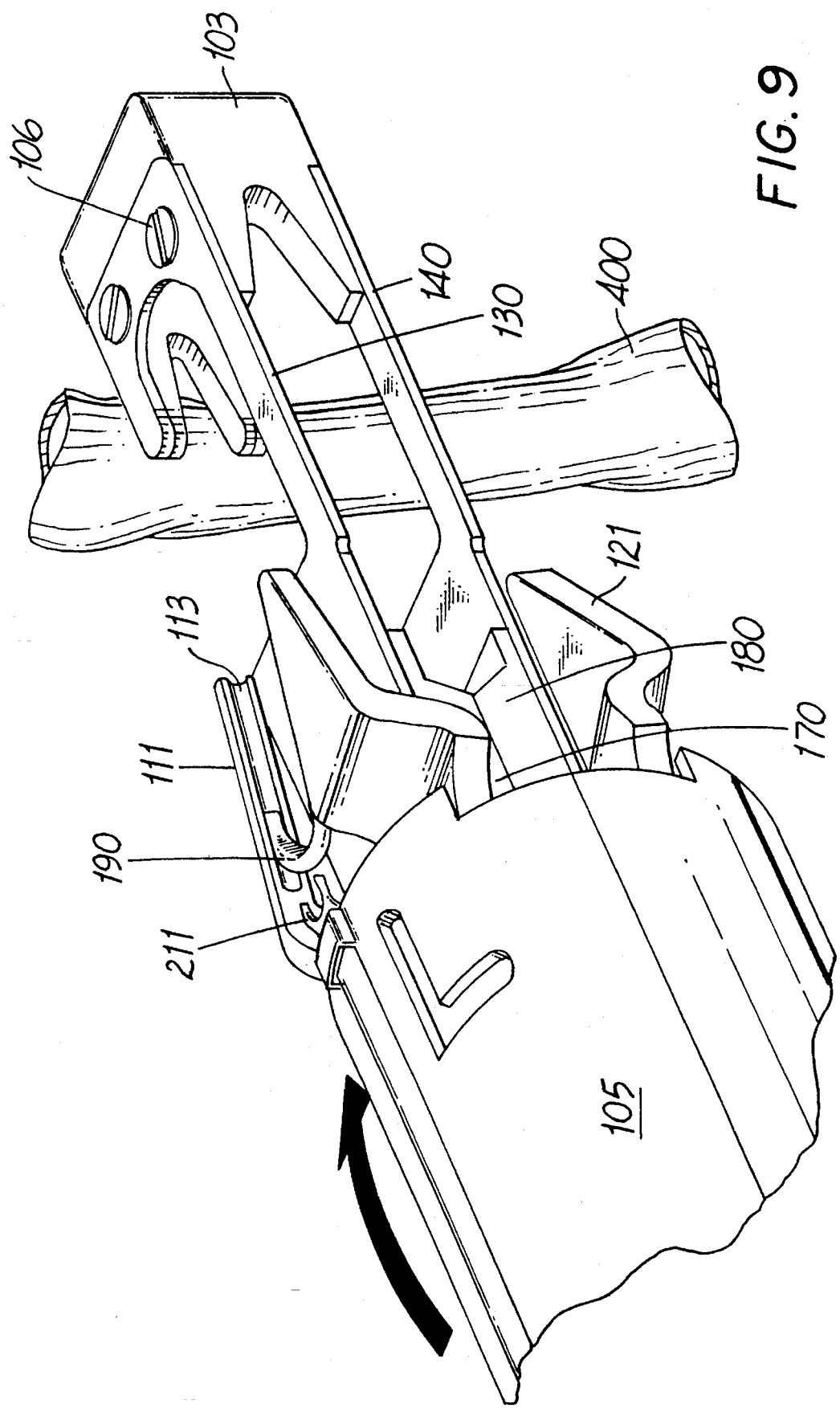
FIGS. 9, 10, 11, 12, 13 and 14 are perspective views respectively illustrating: loading of a clip into the jaws of the apparatus, capture of a tubular structure, moving the tubular structure into position between the jaws of the instrument, closing the jaws of the instrument to apply the clip to the tubular structure, cutting the tubular structure, and release of the tubular structure.

The actuation of the ligating and dividing instrument 100 is illustrated in FIGS. 9 to 14. Referring to FIG. 9, the endoscopic portion of the instrument 101 is inserted through a cannula and positioned such that the operating portion 102 is in proximity to the tissue to be operated upon, i.e., blood vessel 400, as illustrated. The surgeon advances a clip 190 to each of the jaws 111 and 121 by pressing the clip advancing actuator 390 (FIG. 8). The clips slide into slots 113 and 123, respectively.

Figure 10:
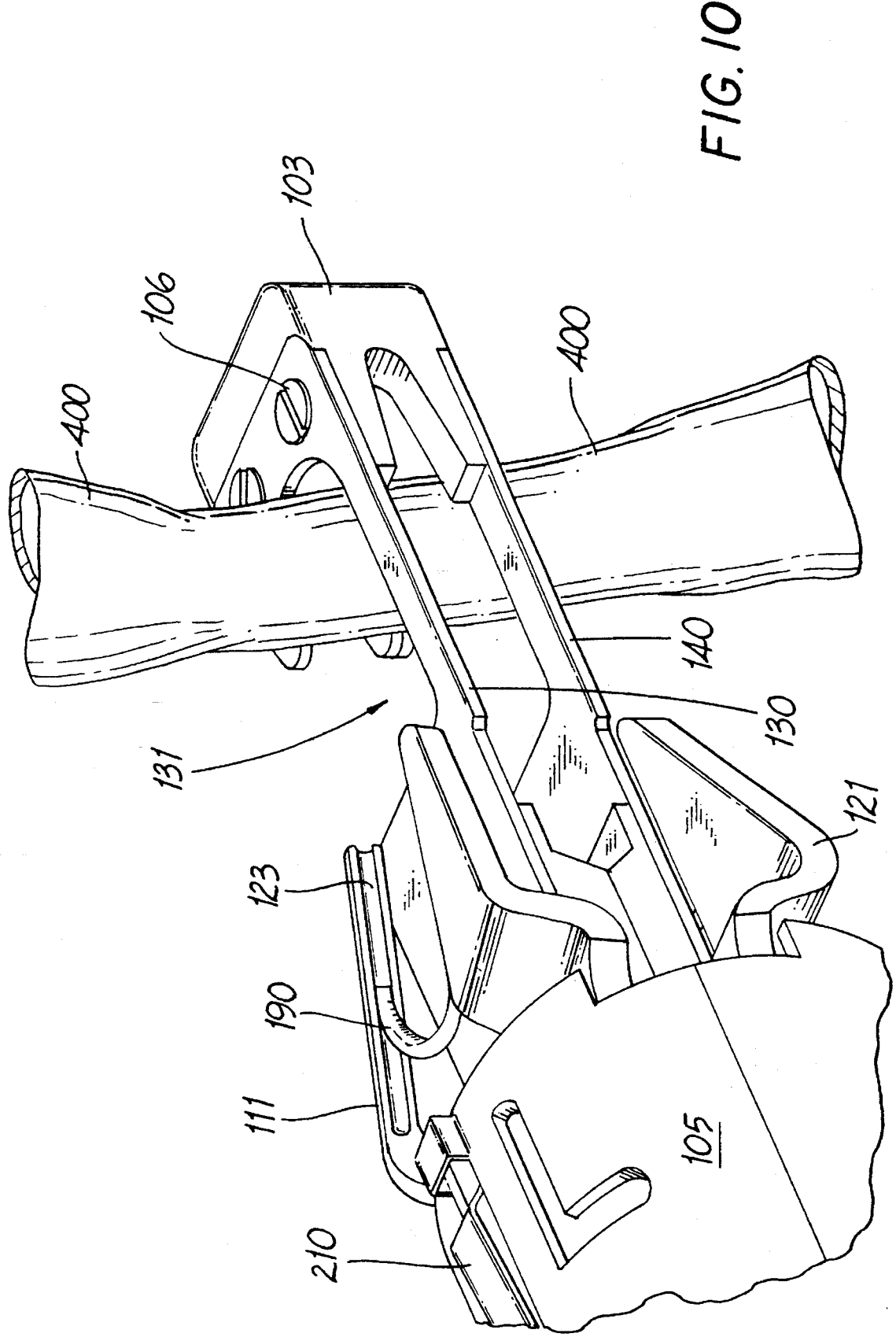

Referring to FIG. 10, the operating portion 102 is maneuvered to position blood vessel 400 in the space 131 defined by the distal hook ends 132 and 142 of hook members 130 and 140.

Figure 11:
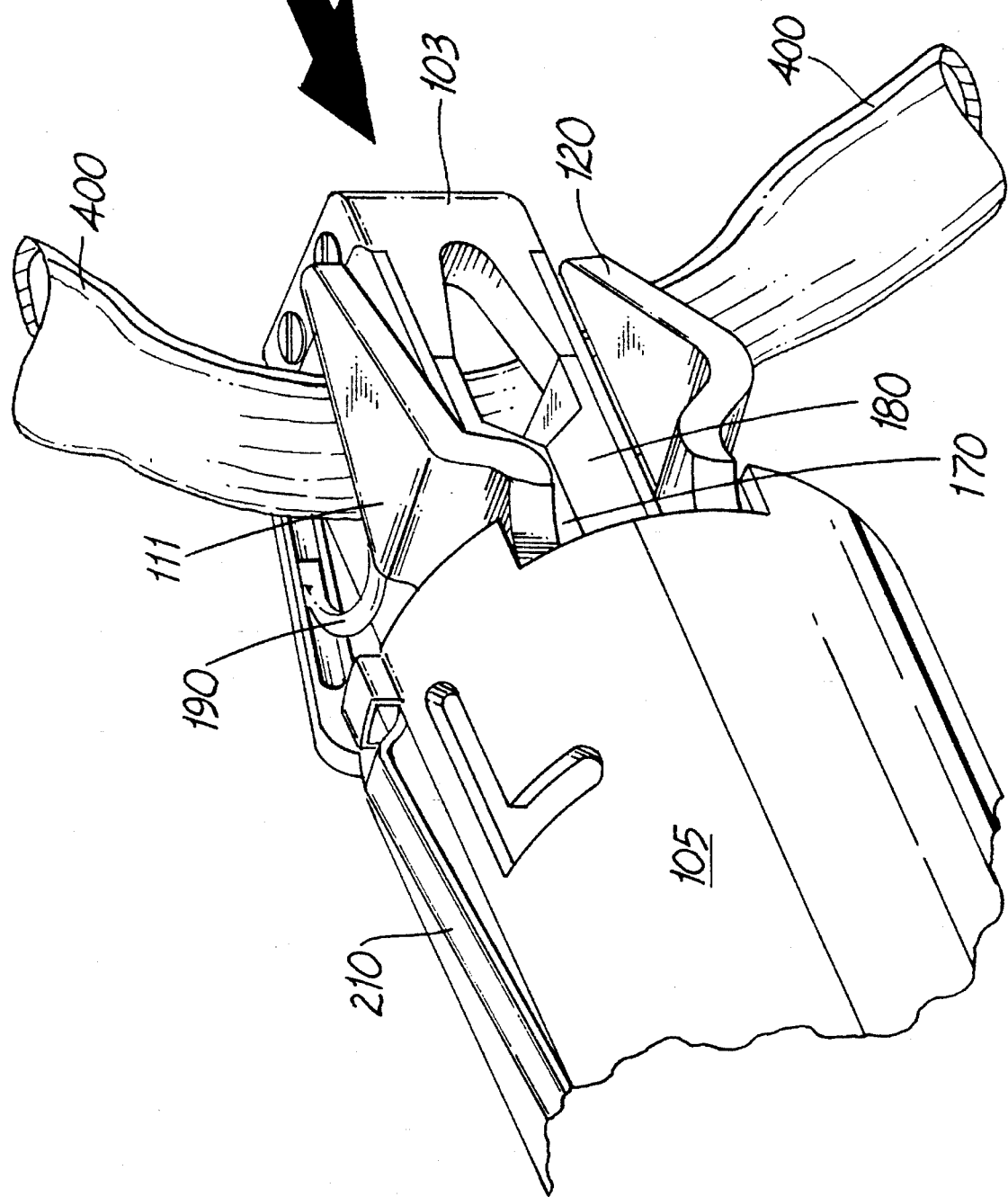

Referring to FIG. 11, the hook members 130 and 140 are retracted to capture blood vessel 400. Retraction of the hook members 130 and 140 is achieved when the surgeon pulls back on hook retracting actuator 380 (FIG. 8). Tissue stops (FIGS. 4 and 5) 171 and 181 provide a proximal barrier to maintain tissue 400 between the pairs of jaws 111 and 121.

Figure 12:
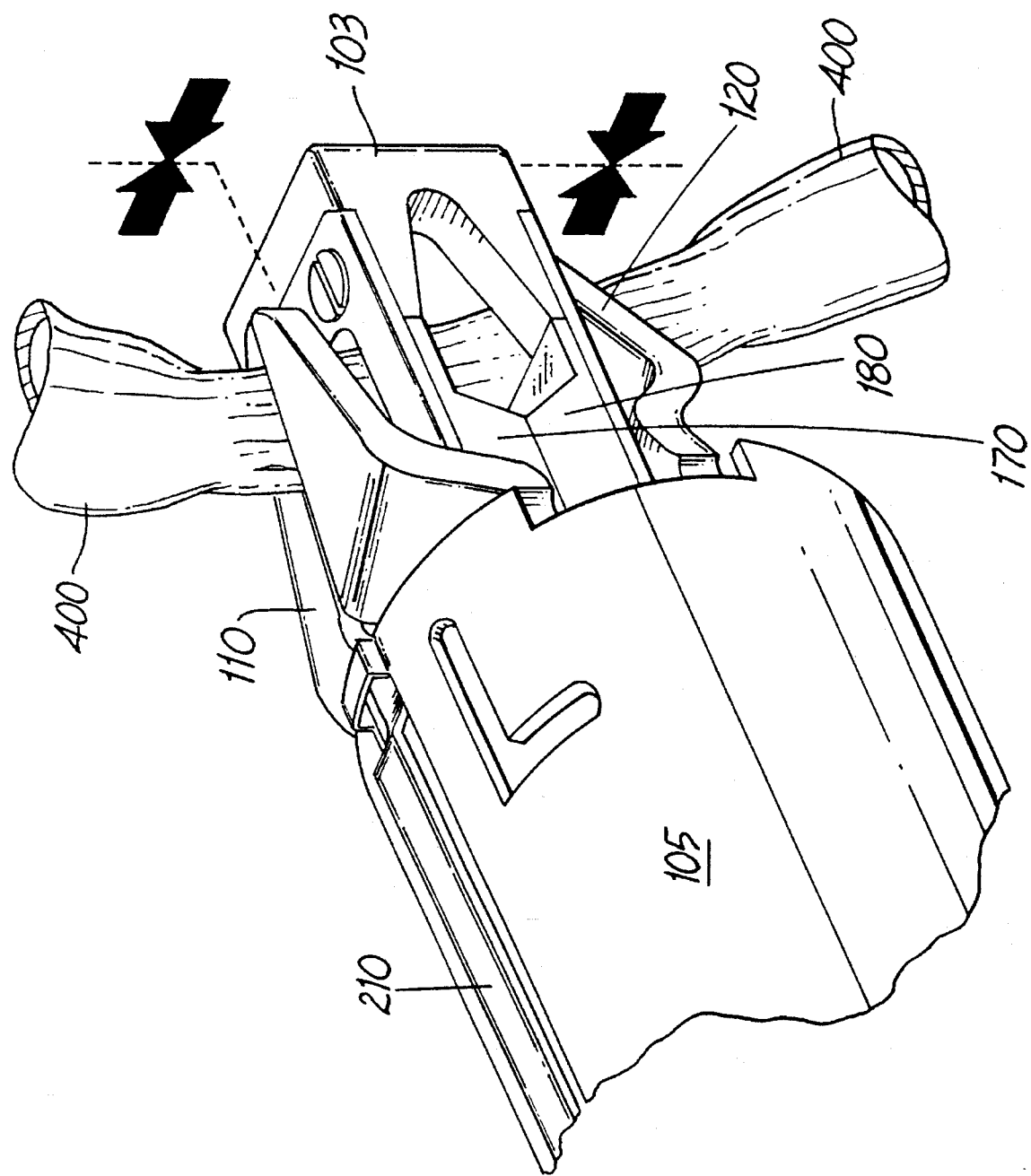

Referring to FIG. 12, the clips 190 are then applied to the blood vessel 400 when the surgeon pulls the trigger 290 (FIG. 8), thereby advancing camming members 150 and 160 and closing jaws 111 and 121.

Figure 13:
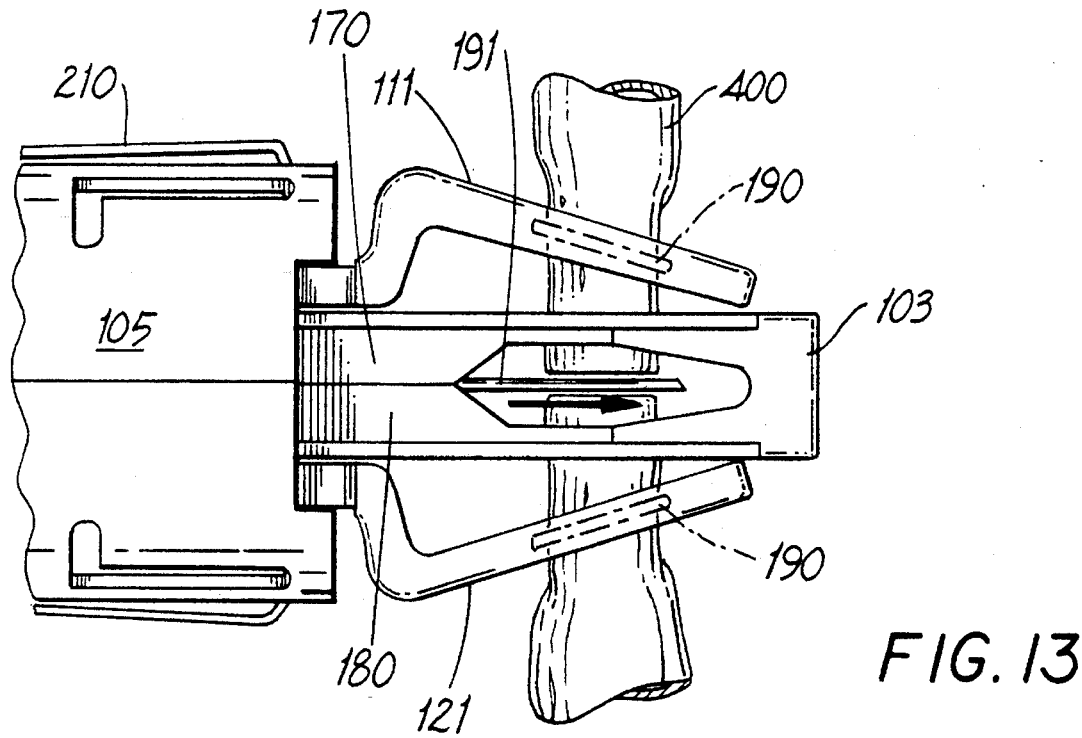

Referring to FIG. 13, the surgeon presses knife advancing actuator 370 (FIG. 8) to push knife 191 forward, thereby dividing blood vessel 400.

Figure 14:
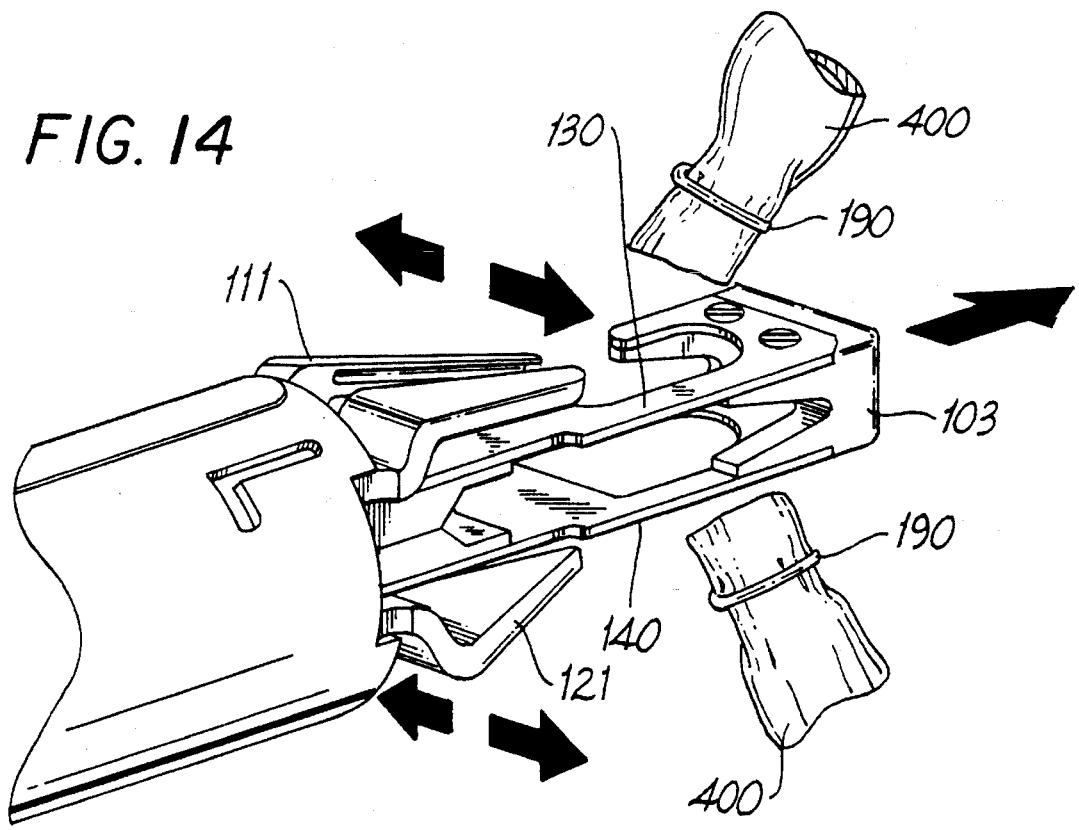

Referring to FIG. 14, the jaws 111 and 121 are opened, the hook members 130 and 140 are advanced, thereby releasing the ligated and divided blood vessel 400.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An apparatus for endoscopically applying surgical fasteners to body tissue, which comprises:

an endoscopic portion having a longitudinal axis and terminating in a distal end for positioning in proximity to the body tissue, and applying means positioned at least partially within said endoscopic portion for simultaneously applying at least two surgical fasteners to the body tissue at spaced apart locations, said applying means being movable at an angle to said longitudinal axis, wherein said fasteners are moved longitudinally for application to the tissue and wherein said endoscopic portion includes a longitudinally extending substantially cylindrical tube for at least partially enclosing said means for applying at least two surgical clips, and said apparatus further including a movable knife for cutting said body tissue.

2. The apparatus of claim 1, wherein said fasteners are surgical clips.

3. The apparatus of claim 2, wherein said applying means comprises two spaced apart clip closing means, and means for distally advancing two clips simultaneously each to a respective one of said clip closing means.

4. The apparatus of claim 3, wherein said clip closing means each comprise a pair of jaws, each jaw being movable with respect to said cylindrical tube between a spaced apart open position for receiving a surgical clip and body tissue therebetween and a closed position for clamping said surgical clip into said body tissue, wherein said apparatus further includes camming means longitudinally movable between a proximal position and a distal position, and said jaws being moved to said closed position in response to movement of said camming means to said distal position.

5. The apparatus of claim 1 wherein said endoscopic portion further includes a tubular housing for at least partially enclosing said means for simultaneously applying at least two surgical fasteners.

6. An apparatus for endoscopically ligating body tissue, which comprises:

an endoscopic portion having a longitudinal axis and including clip closing means at a distal end thereof for applying at least two surgical clips to the body tissue at spaced apart locations, wherein said clip closing means includes first and second pairs of opposing jaws, each jaw being movable between an open position and a closed position and each pair being spaced apart from the other of said pairs, camming means for moving each said jaw from said open position to said closed position, at least one movable knife means for cutting tissue, movable catch means positioned at the distal end of said endoscopic portions, said movable catch means being movable between a distal position and a proximal position, said movable catch means engaging the body tissue and positioning the body tissue for operation by said clip closing means, pusher means for individually advancing at least two surgical clips to said clip closing means, and said endoscopic portion further including a longitudinally extending tube at least partially enclosing and supporting said clip closing means, said pusher means, said catch means, said camming means and said movable knife means.

7. The apparatus of claim 6, wherein said pusher means substantially simultaneously advances two surgical clips.

8. The apparatus of claim 6, wherein said clip closing means substantially simultaneously applies two surgical clips.

9. The apparatus of claim 6, wherein said first and second pair of jaws, in response to movement of a jaw actuation means, are laterally movable between an open position wherein the jaws of each pair are spaced apart a relatively wider distance for receiving a surgical clip and body tissue therebetween, and a closed position wherein said jaws of each pair are in relatively close proximity to each other for closing said clip, each of said jaws possessing at least one camming surface, and wherein the apparatus further includes jaw actuation means including jaw camming means movable between a proximal position and a distal position wherein said camming means closes said jaws.

10. The apparatus of claim 9, wherein each pair of jaws is mounted to a corresponding pair of prong portions of at least one fork member, said pairs of jaws being resiliently biased to said open position.

11. The apparatus of claim 10, wherein said jaws and at least one fork member are of integral construction.

12. The apparatus of claim 9, wherein said apparatus further comprises means for storing a plurality of clips two parallel, longitudinally oriented rows.

13. The apparatus of claim 12, wherein said pusher means include means for moving the furthest clip at the distal end of each of said two rows into position in said clip closing means.

14. The apparatus of claim 13, wherein said means for storing a plurality of surgical clips includes at least one track means for orienting said row of clips.

15. The apparatus of claim 14, wherein said track means includes an elongated first portion oriented longitudinally with respect to the endoscopic portion of this apparatus, and a distal portion for positioning the distally furthest clip of the clip row for insertion into the clip closing means, said distal portion of the track means being resiliently biased to a first position wherein said distal portion is inclined with respect to the first portion of the track means towards the axial center of the endoscopic portion of the apparatus, and said distal portion being resiliently movable to a second position relatively further away from the axial center of the endoscopic portion in response to advancement of the jaw camming means.

16. The apparatus of claim 6, wherein said knife means is positioned for cutting body tissue between said spaced apart locations of the clips.

17. The apparatus of claim 16, wherein said knife means is at least partially enclosed within said longitudinally extending tube.

18. The apparatus of claim 17, further including a non-endoscopic portion which comprises:

a housing, which supports and at least partially encloses a knife actuation means for actuating said knife means, catch actuation means for actuation said catch means, pusher actuation means for actuating said pusher means, and jaw actuation means for closing said clip closing means.

19. The apparatus of claim 18, wherein the knife means comprises:

an elongated member having distal and proximal ends and extending longitudinally through the tube; and, a tissue cutting blade mounted to the distal end of said elongated member, said tissue cutting blade being movable between a distal position and a proximal position.

20. The apparatus of claim 19, wherein said proximal end of said elongated member is connected to the knife actuation means; and, said knife actuation means is distally movable between a proximal position and a distal position in response to user applied pressure.

21. The apparatus of claim 20, wherein the knife actuation means is biased by resilient means to said proximal position.

22. The apparatus of claim 18, wherein the catch means comprises at least two elongated members, each having a distal end portion and a proximal end portion, each member being longitudinally movable between a proximal position and a distal position, each member having a tissue reception space defined by a hook configuration of said distal end portion, said distal end portions being fixedly attached to a spacer member located therebetween, and said proximal end portions being connected to the catch actuation means.

23. The apparatus of claim 22, wherein said elongated members are longitudinally oriented with respect to the tube.

24. The apparatus of claim 23, wherein said catch actuation means comprises a member slidably mounted to the housing, said member being longitudinally movable between a proximal position and a distal position in response to user applied pressure.

25. The apparatus of claim 18, wherein said pusher means comprises at least two elongated members, each being longitudinally movable between a proximal position and a distal position, and each having a distal end portion and a proximal end portion.

26. The apparatus of claim 25, wherein said two elongated members are longitudinally oriented with respect to the tube.

27. The apparatus of claim 26, wherein said distal end portion possesses means for engaging the back of a surgical clip, and said proximal end portion is mounted to the pusher actuation means.

28. The apparatus of claim 27, wherein said pusher actuation means comprises a member slidably mounted to said housing, said member being longitudinally movable between a proximal position and a distal position in response to user applied pressure.

29. The apparatus of claim 28, wherein said pusher actuation means is biased by resilient means to said proximal position.

30. The apparatus of claim 16, further including knife cover means for covering said knife.

31. The apparatus of claim 30, wherein said knife cover means defines a chamber which is in a fixed position relative to the endoscopic portion of the apparatus and through which the knife means is slidably disposed.

32. The apparatus of claim 31, wherein said knife cover means has a proximal end portion which provides mounting means for fixedly mounting said knife cover means to the interior of the endoscopic portion of the instrument, and a distal edge which is configured and positioned relative to the clip closing means to serve as a tissue stop means for preventing body tissue within the clip closing means from moving proximally out of the range of the clip closing means.

33. The apparatus of claim 6 wherein said jaws are movable in a direction transverse to the longitudinal axis of the endoscopic portion.

34. The apparatus of claim 6 wherein said movable catch means is positioned between said first and second pairs of opposing jaws.

35. An apparatus for endoscopically ligating body tissue, which comprises:

an endoscopic portion including clip closing means at a distal end thereof for applying at least two surgical clips to the body tissue at spaced apart locations, wherein said clip closing means includes first and second pairs of opposing jaws, each pair being spaced apart from the other of said pairs, movable catch means positioned at the distal end of said endoscopic portion and between said first and second pairs of opposing jaws to engage the body tissue and position the body tissue for operation by said clip closing means, pusher means for individually advancing at least two surgical clips to said clip closing means, and a longitudinally extending tube at least partially enclosing and supporting said clip closing means, pusher means and catch means, wherein said first and second pair of jaws, in response to movement of a jaw actuation means, are laterally movable between an open position wherein the jaws of each pair are spaced apart a relatively wider distance for receiving a surgical clip and body tissue therebetween, and a closed position wherein said jaws of each pair are in relatively close proximity to each other for closing said clip, each of said jaws possessing at least one camming surface, wherein the apparatus further includes jaw actuation means including jaw camming means movable between a proximal position and a distal position wherein said camming means closes said jaws, and wherein said jaw actuation means comprises at least one elongated member having a distal end portion and a proximal end portion, said distal end portion including at least one edge for contacting the camming surfaces of said jaws and urging said respective pairs of jaws laterally inward to the closed position, said elongated member being longitudinally movable between a distal position wherein said pairs of jaws are cammed to said closed position and a proximal position wherein said pairs of jaws are in said open position.

36. The apparatus of claim 35, wherein said jaw actuation means further includes trigger means connected to the proximal end portion of said at least one elongated member of the jaw actuation means, said trigger means being movable between a jaw opening position and a jaw closing position in response to a user applied force.

37. The apparatus of claim 31, wherein said trigger means is pivotally mounted to said housing such that movement of the trigger means from said jaw opening position to said jaw closing position advances at least one elongated member of the jaw actuation means to the distal position wherein said jaws are cammed closed.

38. An apparatus for endoscopically ligating body tissue, which comprises:

an endoscopic portion including a longitudinally extending tube, clip closing means extending from said longitudinally extending tube for applying at least two surgical clips to the body tissue at spaced apart locations, said clip closing means including first and second pairs of jaws each jaw being movable relative to said tube in response to jaw actuation means between a spaced apart open position and a closed position, knife means for cutting the body tissue at a location between said spaced apart surgical clips, and pusher means at least partially enclosed within said longitudinally extending tube for individually advancing at least two surgical clips to said clip closing means.

39. The apparatus of claim 38, wherein said two surgical clips are simultaneously advanced by said clip pusher means.

40. The apparatus of claim 39, wherein said two surgical clips are simultaneously applied by said clip closing means.

41. The apparatus of claim 38 further comprising movable catch means for engaging the body tissue and moving the body tissue into position for operation by said clip closing means.

42. The apparatus of claim 38 further including seal means for preventing the passage of gases through the apparatus.

43. An apparatus for applying surgical clips to body tissue, which comprises:

a) a frame having a substantially cylindrical portion defining a longitudinal axis and terminating in a distal end;

b) at least one pair of jaws laterally movable between a spaced apart open configuration and a closed configuration;

c) a tissue catch member including two spaced apart hook portions, the tissue catch member being longitudinally movable between distal and proximal positions;

d) a tissue cutter which is longitudinally movable between a proximal position and a distal tissue cutting position, and which is slidably disposed between said two spaced apart hook portions of said tissue catch member; and e) a plurality of surgical clips supported in the apparatus, and a pusher for advancing at least one of the surgical clips to a position between said pair of jaws.

44. The apparatus of claim 43 further comprising a camming member for closing said pair of jaws, said pair of jaws being resiliently biased to said open configuration and moved to said closed configuration in response to distal movement of said camming means.

45. The apparatus of claim 43 wherein said tissue engaging aperture of each said hook portion is J-shaped.

46. The apparatus of claim 43 wherein said tissue cutter comprises a knife blade with a distal cutting edge.

47. An apparatus for applying surgical clips to body tissue, which comprises:
   a) a frame having an elongated substantially cylindrical portion defining a longitudinal axis and terminating in a distal end;
   b) spaced apart first and second pairs of laterally movable jaws;
   c) a tissue catch member longitudinally movable between said first and second pairs of jaws;
   d) a tissue cutter movable between said first and second pairs of jaws; and
   e) a plurality of surgical slips supported in the apparatus, and a pusher for advancing at least one of the surgical clips to a position between said pair of jaws.

48. The apparatus of claim 47 wherein said tissue catch member comprises two spaced apart hook members, each having a tissue receiving aperture.

49. The apparatus of claim 48 wherein said tissue cutter is movable between said spaced apart hook members.

50. The apparatus of claim 49 wherein said tissue cutter is longitudinally movable.

51. The apparatus of claim 50 wherein said tissue cutter has a distal knife edge.

52. The apparatus of claim 48 wherein said tissue receiving apertures are J-shaped.

53. The apparatus of claim 47 wherein each pair of said jaws are resiliently biased to a spaced apart open configuration and moved to a closed configuration in response to the distal movement of a camming member.

* * * * *